US00PP29201P2

(12) United States Plant Patent
Engelke et al.

(10) Patent No.: US PP29,201 P2
(45) Date of Patent: Apr. 3, 2018

(54) ZOYSIAGRASS PLANT NAMED 'TD2013'

(50) Latin Name: ***Zoysia matrella* (L.) Merr.**
Varietal Denomination: TD2013

(71) Applicants: Milton Charles Engelke, Lebanon, OR (US); Virginia Gail Lehman, Lebanon, OR (US)

(72) Inventors: Milton Charles Engelke, Lebanon, OR (US); Virginia Gail Lehman, Lebanon, OR (US)

( * ) Notice: Subject to any disclaimer, the term of this patent is extended or adjusted under 35 U.S.C. 154(b) by 0 days.

(21) Appl. No.: 15/530,064

(22) Filed: Dec. 1, 2016

(51) Int. Cl.
*A01H 5/12* (2018.01)

(52) U.S. Cl.
USPC ..... Plt./390

(58) Field of Classification Search
USPC ..... Plt./390
See application file for complete search history.

*Primary Examiner* — Annette H Para

(57) ABSTRACT

An asexually reproduced variety of perennial zoysiagrass with a unique combination of morphological characters including medium leaf texture, sparse inflorescence production, early spring greenup and good canopy color retention in the fall.

2 Drawing Sheets

Latin name of the genus and species of the plant claimed: The present invention relates to the genus and species *Zoysia matrella* (L.) Merr.

Variety denomination: 'TD2013'.

CROSS-REFERENCE TO RELATED APPLICATIONS

"Not Applicable"

STATEMENT REGARDING FEDERALLY SPONSORED RESEARCH OR DEVELOPMENT

"Not Applicable"

BACKGROUND OF THE INVENTION

Field of Invention

The present invention relates to a new and distinct asexually reproduced variety of perennial zoysiagrass (*Zoysia matrella* (L.)) Merr.

BRIEF SUMMARY OF THE INVENTION

This invention relates to a new and distinct perennial zoysiagrass cultivar identified as 'TD2013' zoysiagrass (herein referred to as 'TD2013'). The inventors, Milton C. Engelke and Virginia G. Lehman discovered 'TD2013' under cultivated conditions in turf plantings near Lebanon, Oreg. 'TD2013' was identified in year 2013 as a distinctly different vegetative patch or clonal plant differing from the surrounding plants in zoysiagrass variety trials. 'TD2013' showed less seedheads than 'Diamond' (U.S. Plant Pat. No. 10,636), and both earlier greenup in the spring, and longer color retention in the fall than 'Diamond'. The inventors asexually reproduced 'TD2013' by taking vegetative cuttings of stolons and rhizomes, cutting the rhizomes and stolons into segments, each with a vegetative bud, and rooting them in potting media. 'TD2013' zoysiagrass will be used as a turfgrass suitable for home lawns, sports fields, golf courses, and soil stabilization.

For purposes of registration under the "International Convention for the Protection of New Varieties of Plants" (generally known by its French acronym as the UPOV Convention) and noting Section 1612 of the Manual of Plant Examining Procedure, it is proposed that the title of the invention is Zoysiagrass plant named 'TD2013'.

BRIEF DESCRIPTIONS OF THE ILLUSTRATIONS

FIG. 1. Tiller of 'TD2013' zoysiagrass.
FIG. 2. Inflorescence of 'TD2013' zoysiagrass.

COMPLETE DESCRIPTION OF THE VARIETY

'TD2013' was characterized in greenhouse and field conditions. 'TD2013' is a unique variety of zoysiagrass (*Zoysia matrella* (L.)) Merr. that was discovered under cultivated conditions.

The inventors, Milton C. Engelke and Virginia G. Lehman, discovered 'TD2013' near Lebanon, Oreg. in turf plantings designed to identify strengths, weaknesses, and purity of zoysiagrass experimental lines. In 2011, Milton C. Engelke visited a cemetery near Buford, S.C., and obtained several vegetative samples of what appeared to be strains of two to three different zoysiagrasses. The parents of the collected strains are unknown.

The vegetative samples were planted in Lebanon, Oreg., and based on the distinction of propagules from one of the samples, 'TD2013' was identified in year 2013 as a distinctly different vegetative patch or clonal plant. 'TD2013' showed less seedheads than 'Diamond' (U.S. Plant Pat. No. 10,636) and both earlier greenup in the spring, and longer color retention in the fall than 'Diamond'. The notable early spring greenup of 'TD2013' and the extended fall color rentention are unique in the zoysiagrasses known to this time. The plants were evaluated in Oregon in USDA Plant Hardiness Zone 8b. The inventors asexually reproduced 'TD2013' in Lebanon, Oreg. by taking vegetative cuttings of stolons and rhizomes, cutting the rhizomes and stolons into segments, each with a vegetative bud, and rooting them in potting media. Planting of the rooted material provided planting stock for studying performance and for comparison of morphological characters after propagation. 'TD2013' has been propagated by rhizomes, stolons, tillers, and sod.

Asexually reproduced plants of 'TD2013' have remained stable and true to type through successive generations of propagation. No seedling establishment from 'TD2013' has been noticed in either greenhouse or field studies.

'TD2013' is a perennial zoysiagrass that spreads by both stolons and rhizomes. Characteristics of 'TD2013' measured in 2015 were taken from plants that were approximately 8 months in age. The greenhouse was located near Lebanon, Oreg., with a nighttime low temperature of 50 degrees F., and daytime high of 80 degrees F., and a minimum soil temperature of 77 degrees F. The plants were grown under natural day length without supplemental lighting. The plants were fertilized with the equivalent of 1 pound of actual N per month, using a soluble fertilizer of 20-20-20 in four equal soluble applications per month.

'TD2013' has a medium leaf texture, with a wider leaf than 'Diamond' (Table 1).

'TD2013' has a few sparse long leaf hairs, in contrast to 'Zorro'(U.S. Plant Pat. No. 14,130) which has many leaf surface hairs (Table 2). 'TD2013' has shown color ratings in early spring in California higher than 'Zorro' (Table 4), but not different from 'Zorro' when rated in September.

'TD2013' has not shown susceptibility to the zoysiagrass mite when tested at Poteet, Tex., where susceptible varieties have shown the coachwhip leaf symptoms of the mite.

TD2013 has shown susceptibility to cool-season brown patch disease (*Rhizoctonia* sp.) when grown near Oxnard, Calif. 'TD2013' has shown good turfgrass performance and temperature adaptation when tested as far north as Willamette River Valley of western Oreg., USDA hardiness zone 8b, which would extend the area of adaptation for 'TD2013' into the central transition zone including Oklahoma, southern Illinois and Indiana, and south through Mexico. 'TD2013' will be limited only by winter survival in colder regions, and has shown good winter survival in field plantings in Oregon during the winter of 2013-14 and 2014-15. 'TD2013' is similar to most medium textured zoysiagrasses in water use demands as shown in test situations in Lebanon, Oreg., compared to 'Cavalier' (U.S. Plant Pat. No. 10,778), 'Zorro', and 'Diamond'. 'TD2013' is adapted from sandy to heavier loam soil textures and from slightly acid to slightly alkaline soil pH.

TABLE 1

Leaf blade widths and lengths and texture class of selected zoysiagrass cultivars, measured under greenhouse conditions in Lebanon, OR, 2015.

| Variety | Length, 2nd youngest crown leaf cm | Width, 2nd youngest crown leaf mm | Leaf Texture Class Rating |
|---|---|---|---|
| 'TD2013' | 3.3 | 1.9 | Medium |
| 'Diamond' | 3.3 | 1.5 | Fine |

TABLE 2

Adaxial leaf hair presence or absence of selected zoysiagrass cultivars, measured under greenhouse conditions in Lebanon, OR, 2015.

| Variety | Leaf hair, adaxial Presence/ Number |
|---|---|
| 'TD2013' | Sparse |
| 'Diamond' | Absent |
| 'Zorro' | Many |

TABLE 3

Stolon characters of 'TD2013', measured under greenhouse conditions in Lebanon, OR, 2015.

| Variety | Thickness 1st youngest stolon node mm | Thickness 2nd youngest stolon node mm | Stolon Internode length, 1st to 2nd node cm | Stolon Internode length, 2nd to 3rd node cm | Stolon Internode length, 3rd to 4th node cm |
|---|---|---|---|---|---|
| 'TD2013' | 0.9 | 1.05 | 0.73 | 0.85 | 0.83 |

TABLE 4

Turf quality ratings taken February 2016 in Oxnard, CA. Turf mowed at fairway heights.

| Variety | Color ^ | Quality # |
|---|---|---|
| 'TD2013' | 4.7 | 5.7 |
| 'Zeon' | 4.3 | 2.3 |
| Zorro' | 2.3 | 1.3 |
| CV | 32 | 21 |
| Lsd, p = 0.05 | 1.88 | 2.3 |

^ Color rated on a scale of 1-9, 9 = darkest green.
Quality rated on a scale of 1-9, 9 = best quality.

TABLE 5

Turf quality ratings taken in September in Oxnard, CA in 2016. Turf mowed at fairway heights.

| Variety | Color ^ | Smoothness # |
|---|---|---|
| 'TD2013' | 7.3 | 5.7 |
| 'Zeon' | 6.7 | 6.7 |
| Zorro' | 7.3 | 7 |
| CV | 9.3 | 31 |
| Lsd, p = 0.05 | 1.1 | 2.4 |

^ Color rated on a scale of 1-9, 9 = darkest green.
Smoothness rated on a scale of 1-9, 9 = most smooth.

TABLE 6

Spring Greenup and Fall Color ratings taken near Lebanon, OR, in 2013-14 and 2014-2015.

| Variety | Early spring greenup rating | Mid-Spring greenup rating | Fall Color Retention rating # |
|---|---|---|---|
| 'TD2013' | 4 | 9 | 5 |
| 'Diamond' | 1 | 4 | 1 |
| 'Zorro' | 1 | 3 | 1 |

* Greenup rated on a scale of 1-9, 9 = earliest greenup;
Early date = approximately 3rd week in March. Mid-spring rated in mid-April.
Fall color retention rated on a scale of 1-9, 9 = green longer in the fall.

COMPLETE BOTANICAL DESCRIPTION OF THE VARIETY

Origin: 'TD2013' is a cultivar of a single clone of zoysiagrass discovered under cultivated conditions in a Lebanon, Oreg. planting of zoysiagrass variety and experimental plots, with some of the plots derived from a collection of vegetative plugs from a cemetery near Buford, S.C. The parents of the collected plugs are unknown. 'TD2013' was identified in year 2013 as a distinctly different vegetative patch or clonal plant. 'TD2013' differed from the surrounding plants in less seedheads than 'Diamond' (U.S. Plant Pat. No. 10,636) when tested in Oregon, and both earlier spring greenup and fall color retention than surrounding grasses. TD2013 has shown to produce a prolific number of seedheads in the Fall of the year when grown near Oxnard, Calif., latitude of 34.2.

Classification: *Zoysia matrella* (L.) Merr.

Growth habit: 'TD2013' is a perennial plant that spreads by stolons and rhizomes and produces a dense, fine textured turfgrass. Seldom producing an inflorescence in Oregon, the inflorescence of 'TD2013' is a terminal spike-like raceme, with spikelets on short pedicels.

Leaf blade: Rolled in the bud, flat surface.

Leaf blade pubescence: Very sparse, adaxial, occasional long hairs, mostly 1 to 1.25 mm long, but up to 1.5 mm in length.

Leaf margin pubescence: Barbellate margins, up to 0.05 mm long, with a frequency of 4 per mm. 'Diamond' has some barbellate margin to a very small degree, but not as prominent or regular as 'TD2013', occurring every 2.5 mm in distance along the leaf.

Leaf sheath pubescence: Absent except for long hairs at mouth of sheath, and a ring of short hairs inside the sheath where it attaches to the stem; 'TD2013' mean length sheath mouth hairs at side of sheath: mostly 1 mm, few at 2.1 mm, and seldom up to 2.5 mm; inside sheath ring of hairs: 0.2 mm.

Leaf blade margin: 'TD2013'=slight roughness;

Leaf blade veins: Prominent.

Leaf blade flexibility (softness): Medium stiff compared to 'Diamond' with a stiff leaf.

Vegetative leaf, 2nd youngest vegetative leaf:

*Blade length range*.—'TD2013': 3.1 to 3.5 cm, mean length: 3.3 cm.

*Blade width mean*.—'TD2013': 1.5 mm to 2.3 mm, mean width: 1.9 mm.

Sheath length, 4$^{th}$ youngest vegetative leaf:

*Mean length 'TD*2013'.—23 mm.

Stolon leaf angle, third youngest leaf: 'TD2013': 85; 'Diamond': 52 (by reference).

Inflorescence characters:

*Culm total length, including floral area to node below flag leaf*.—58 mm. Length of stem of inflorescence: 44 mm. Floral area length: 14 mm.

*Culm width, stem thickness, base of floral area*.—0.55 mm.

*Anther length*.—1.2 mm.

*Floret* (*seed*) *length*.—Range 2.5 to 2.75 mm.

*Floret* (*seed*) *width*.—Mean of 0.7 to 0.8 mm.

*Pedicel length*.—2.0 mm.

*Flag leaf length*.—'TD2013': 5 mm.

*Flag leaf width*.—'TD2013': 0.95 mm.

Mature plant height, unmown in greenhouse, vegetative leaves (not including inflorescence):

'*TD*2013'.—4.5 cm; compared to 'Diamond' at 9 cm.

Mowing height as turf: Optimum height, field trials, 'TD2013': 12 to 90 mm; Diamond: 3-13 mm.

Color notations, vegetative characters, based on The R.H.S. Colour Chart (light quality, photoperiod, and general growth of the plants affect color notations):

*Leaf blade color adaxial leaf surface*.—137 C green.

*Leaf blade color abaxial leaf surface*.—137C green.

*Stolon color*.—159 B orange-white, 138 B green.

Color notations, floral characters, based on The R.H.S. Colour Chart (light quality, photoperiod, and general growth of the plants affect color notations):

*Culm stalk*.—144 A yellow-green.

*Stigma*.—158 B greyed yellow white.

*Anthers, mature, dried*.—160 B greyed yellow with 187 A greyed purple.

Turf quality in August (rated 1-9, 9 best), Lebanon, Oreg: 'TD2013': 6; 'Zorro': 5.

REFERENCES CITED

U.S. Patent Documents

November, 2002 Doguet, D. U.S. Plant Pat. No. 13,166. 'Zeon' zoysiagrass

July, 1997 Engelke, M. C. U.S. Plant Pat. No. 10,778. 'Cavalier' zoysiagrass

October, 1998 Engelke, M. C. U.S. Plant Pat. No. 10,636. 'Diamond' zoysiagrass

July, 2002 Engelke, M. C. U.S. Plant Pat. No. 14,130. 'Zorro' zoysiagrass

We claim:

1. A new and distinct variety of zoysiagrass plant, substantially as described and illustrated herein, characterized particularly by a unique combination of morphological characters.

* * * * *

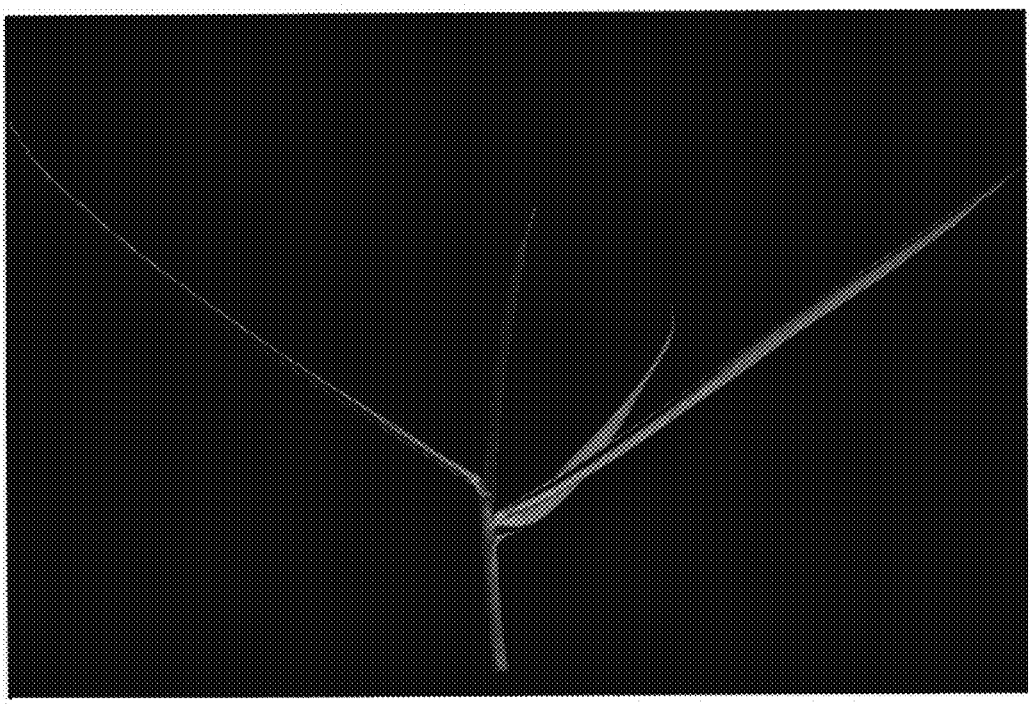
Figure 1. Tiller of '2013' zoysiagrass.

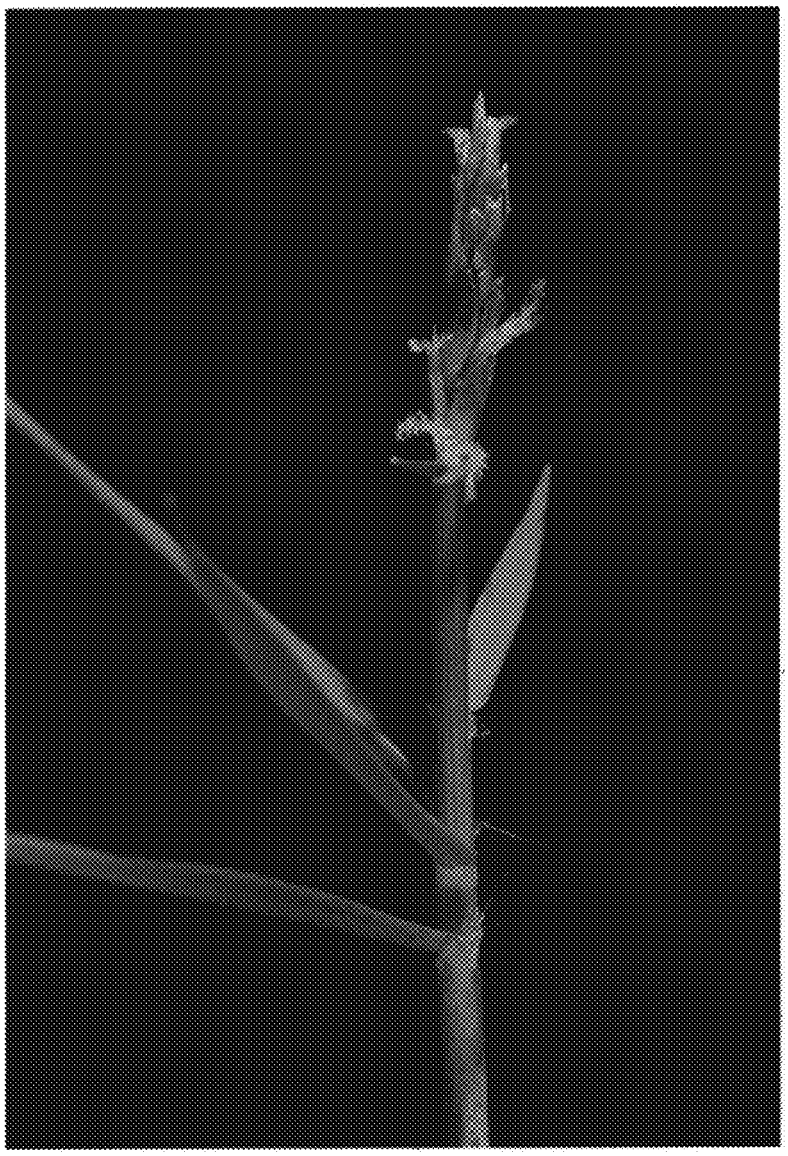
Figure 2. Inflorescence of '2013' zoysiagrass.